United States Patent [19]
Becker

[11] Patent Number: 5,546,792
[45] Date of Patent: Aug. 20, 1996

[54] COMPUTERIZED SONIC PORTABLE TESTING LABORATORY

[75] Inventor: Harold L. Becker, 18906 Grosbeak, Tomball, Tex. 77375

[73] Assignee: Harold L. Becker, Tomball, Tex.

[21] Appl. No.: 363,274

[22] Filed: Dec. 22, 1994

[51] Int. Cl.⁶ ............................ G01N 33/28; G01N 29/02
[52] U.S. Cl. ...................... 73/64.53; 73/64.42; 324/698; 356/70
[58] Field of Search ................... 73/54.41, 61.41, 73/61.43, 61.44, 61.45, 61.48, 61.49, 61.75, 61.79, 64.42, 64.43, 64.53, 596, 597, 151, 155, 64.41; 356/72, 70, 436; 324/698, 71.1, 693; 250/301, 227.11, 573

[56] References Cited

U.S. PATENT DOCUMENTS

| | | | |
|---|---|---|---|
| 2,203,720 | 6/1940 | Dale | 356/436 |
| 2,283,429 | 5/1942 | Ennis | 73/155 |
| 2,671,323 | 3/1954 | Richert | 73/151 |
| 2,699,675 | 1/1955 | Buck et al. | 73/155 |
| 3,075,113 | 1/1963 | Soar | 313/17 |
| 3,130,808 | 4/1964 | Walker, Jr. et al. | 73/155 |
| 3,647,300 | 3/1972 | Skala | 356/73 |
| 4,201,471 | 5/1980 | Pitt et al. | 356/73 X |
| 4,754,839 | 7/1988 | Gold et al. | 73/151 X |
| 5,237,857 | 8/1993 | Dobson et al. | 73/151 X |
| 5,247,828 | 9/1993 | Candau et al. | 73/64.42 |
| 5,402,241 | 3/1995 | Jeannotte et al. | 356/436 |

*Primary Examiner*—Michael J. Brock
*Attorney, Agent, or Firm*—Paul I. Herman

[57] ABSTRACT

A portable sonic testing device for the testing of waxy and emulsified fluids, utilizing variations in sound wave propogation, light propogation, and changes in electrical resistance in the liquid, all over a range of temperatures and chemical treatment conditions. The patent also discloses equations used to derive additional information from the output of the device.

17 Claims, 2 Drawing Sheets

COMPUTERIZED SONIC PORTABLE TESTING LABORATORY

BACKGROUND OF THE INVENTION

The invention related to a device that determines characteristics of fluids, by first measuring variations in the fluid's electrical resistance, translucence, sonic properties, over a range of temperatures or time or both, then by transmitting the generated information to a data logger and computer, where the information is compared to standard curves. This equipment can be made fully portable, so that it can be taken to locations away from laboratories, and has obvious applicability in oilfield applications. The invention further relates to a method for selecting chemicals to modify the fluid's measured characteristics.

Systems carrying oil field production fluids, refinery fluids, and other industrial fluids, containing either an oil or water phase, or both, are susceptible to various chemical related problems, including emulsion formation, wax deposits, scale formation, and asphaltene deposits, in either static or dynamic systems. Entire laboratories are devoted to the evaluation of, and treatment of these problems to reduce their economic impact on the systems. Many of these laboratories have large numbers of highly trained specialists, very expensive scientific equipment, and require large budgets to operate.

Emulsions are complex surface phenomena which results from the interaction of naturally occurring surfactants in multi-component physical systems. Emulsions can be formed as water-in-oil, or oil-in-water mixtures, and the internal phase droplets can range in size from 50 microns, to 0.05 microns. The most stable emulsions have droplets of smaller size. Naturally occurring surfactant which stabilize the emulsion include, but are not limited to, fatty acids, naphthinic acids, fatty organic salts, and other break-down products of bio-molecules.

Emulsions are not desirable in oilfield production, as the purchasers of the production want to purchase oil without any water. Hence, emulsions are treated on-site to separate the water from the oil. Emulsions can be de-stabilized by the addition of synthetic surfactant, salts, or heat; dilution of the water or oil phase; and the use of electro-static grids. Typical demulsification testing is done empirically, by adding various additives to samples of the emulsion, agitating, and then visually observing the amount of water separated from the emulsion through a set amount of time. In the case of the oil-in-water emulsion, a turbidimeter may be used. Demulsification testing is notorious because of the difficulty in generating consistent test results, as all samples are manipulated by hand, and all measurements made by visual observation.

Natural oils, petroleum crude oils, and animal derived oils often contain waxes. Waxes tend to crystallize in these oils when the temperature drops below their respective melting points. These crystallized waxes lose their solubilities in the oil, and network to create larger aggregates which can solidify or gel the oil, or the wax crystals precipitate from the oil. These crystals often form deposits in the system in which they are contained, and cause various physical and mechanical problems (e.g., deposition of solids in storage tanks, deposits in transfer lines, solidification or gelling of the oil, pipeline ruptures due to overpressurization, etc.). Wax problems may be corrected with the use of dispersants, crystal modifiers, or combinations of each. Testing used to determine the extent of the problem and to test possible beneficial additives is performed empirically using rheological analysis, pour point testing (ASTM D-97), cloud point testing, cold finger testing, and other physical-chemical tests, with the tester trying any number of possible additives and visually observing the changes in the sample. Obviously, the tester cannot be sure he has selected the optimum product by this method unless he tests all possible additives, which can be a time-consuming process.

Scale deposition in non-homogeneous systems (e.g., oil-in-water emulsions, and water-in-oil emulsions) does occur, and scale deposition also occurs in high brine, water-only systems. Scale testing may be conducted by several methods, but the most common methods involve the heating of fluids from the field or synthetically produced approximations and measuring the deposits formed. Once the scale crystals are formed, the specific scale can be identified by methods such as X-ray crystallography or atomic absorption. Scale problems may be treated using inorganic salts, polymeric acids, or phosphate esters, which can interfere with the normal crystallization process of the scale crystals.

Asphaltenes are complex, hetero-atomic, polar, macrocyclic, compounds containing carbon, hydrogen, sulfur and oxygen. Asphaltenes occur in crude oils. Resin and maltene precursors of the asphaltenes act as peptizing agents in virgin crude oils to stabilize a dispersion of micelles. When mechanical or chemical forces become sufficiently great, these stabilizing species are lost and the destabilized asphaltenes become susceptible to interaction and aggregation resulting in deposition of asphaltene macro-particles. Testing for asphaltenes, is most effectively accomplished by core tests, in which a suspension of the asphaltenes are pumped through a core-rock sample, and pressure build-up measured. Xylene, toluene or other aromatic solvents have been used for many years for the removal of asphaltenes.

The invention disclosed herein is a testing device capable of determining key fluid characteristics under a variety of controlled conditions. This invention also includes an improved method for selecting treatment additives, utilizing the inventive device.

SUMMARY OF THE INVENTION

The invention relates to testing equipment that can collect key data about a fluid, including changes in electrical resistance, translucence, and sonic properties, all over a range of temperatures or time. This information is sent to an output device, such as a data-logger, a computer, or a strip recorder.

In the case of waxy crudes, once the desired information is collected, curves showing time v. temperature can be generated by the computer from the data which can be compared to standard curves contained in a database, and thereby a determination made of the distribution of waxes, based on carbon length and percentage in the crude. Using this information, an additive can quickly be selected, based on its known effectiveness on particular carbon-lengths of waxes.

In the case of emulsion testing, a determination can be made based on the output to the-strip recorder of how quickly and efficiently the emulsion is breaking. Further, using the inventive device allows for much greater repeatability and detailed analysis of the performance of various additives.

In the case of scale or asphaltene testing, the device can be used to decide with great accuracy which treatment additives provide maximum scale reduction or asphaltene deposition reduction, respectively.

Further, the inventive device can be used to provide computerized control of treatment systems to optimize the various chemical treatment systems, by continuously monitoring a sidestream of fluids and altering the volume of additive added to the fluids based on measured characteristics.

Further, the inventive device can be built as a fully portable unit, to allow testing on-site, wherever the location.

DETAILED DESCRIPTION OF THE INVENTION

Figure 1:
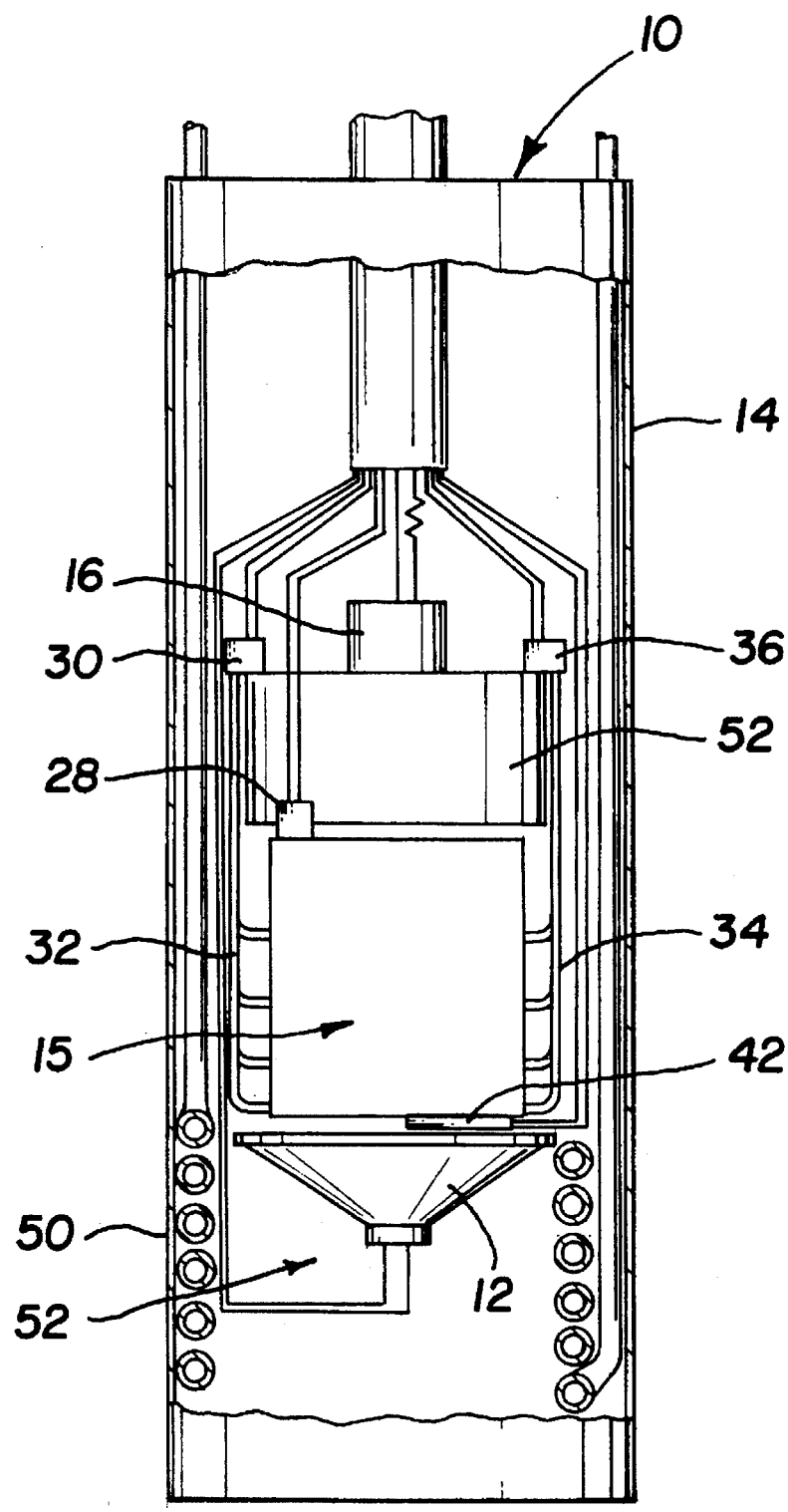
FIG. 1 is a cutaway view of a probe embodying features of the present invention.
Figure 2:
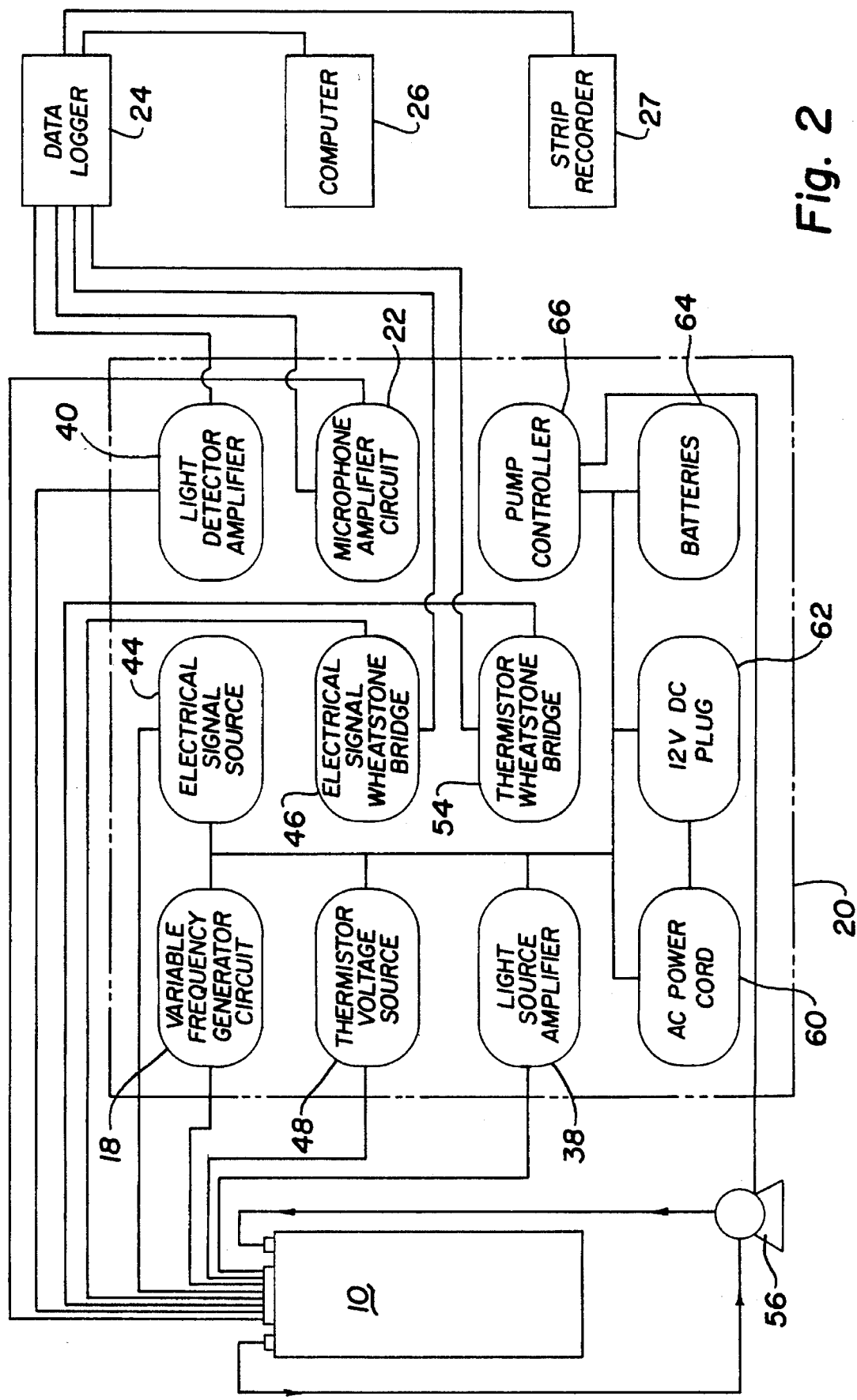
FIG. 2 is a schematic diagram of a control box embodying features of the present invention.

The invention uses a probe 10 constructed of molded epoxy resin to house a series of measuring devices to obtain data about the fluid in which it is immersed (see FIG. 1). The probe 10 comprises a cylinder 14, preferably 18 centimeters in length, the cylinder 14 being completely sealed except for two large openings on opposite sides of the diameter of the cylinder 14, both near the center of the length of the cylinder 14, thereby defining a sample cavity 15. A speaker 12 is positioned within the cylinder 14 in 180 degree opposition to a microphone 16, also within the probe 10 (i.e., the microphone 16 and speaker 12 are facing each other). The speaker 12 is driven by a variable frequency generator circuit 18 which is preferably contained in a control box 20 (see FIG. 2), though it could be contained in the probe. The microphone signal is amplified by a separate microphone amplifier circuit 22, also preferably contained within the control box 20. The amplified signal from the microphone amplifier circuit 22 is sent to a data-logger 24 as a voltage signal. From there, the signal can be further analyzed by a series of algorithms contained in a separate computer program, stored in a computer 26. The signals can also be output to a strip recorder 27, or other output device. Fluids contained within the probe cylinder 14 alter the nature of the propagated sound waves. The alteration of sound waves passing through the fluid varies with temperature. That is, for instance, when a heated sample is cooled sufficiently, wax crystals begins to form, which alter how the sound waves move through the fluid. These changes can be recorded over a range of temperature, preferably starting at a relatively high temperature and proceeding to a relatively low temperature.

The temperature of the fluid in the probe can be measured by measuring the temperature of the bulk fluid. But preferably, each probe 10 preferably contains a thermistor 28, to measure temperature, allowing the temperature of the fluid to be measured very close to the speaker 12 and microphone 16. A signal is sent from a thermistor voltage source 48 to the thermistor 28. The signal is then returned to a Wheatstone bridge 54, which transforms the signal. Both the thermistor voltage source 48 and the Wheatstone bridge 54 are preferably stored in the control box. The new signal is then sent to the data-logger 24. The temperature information is combined with the sonic data to help generate characteristic curves of the fluid. These curves can be used to help determine characteristics of the fluid, as well as aid in the selection of additives, as discussed below.

The probe 10 also can have a system for measuring the tranmissivity of light through the fluid. This system comprises an LED source 30, a source light pipe 32, an opposed light detector pipe 34, and a Cadmium Sulphide detector 36. The opposed light source/detector pipes 32 and 34 are each piped to multiple levels within the probe cylinder 14 to measure light transmission through the fluid. The LED source 30 is driven by a light source amplifier 38 preferably contained within the control box 20. The signal generated by the Cadmium Sulphate detector 36 is sent to the light detector amplifier 40 and the output signal from the light detector amplifier 40 is sent to the data-logger 24. This data, when combined with the temperature data, can aid in detecting the onset of cloud points in the fluid, as well as helping determining how well broken an emulsion is, since as the emulsion breaks the fluid become more translucent. This system is very useful for emulsion testing, because the testing can be tightly controlled and results precisely measured, and transmissivity results are very repeatable, unlike current test methods in the field.

Also contained within the cylinder 14 can be conductivity bridge 42. The conductivity bridge 42 receives an electrical signal from a signal source 44, and the returning signal is sent to a Wheatstone bridge 46, which converted the signal, and the new signal is sent the data-logger 24. This data can be used to also detect the extent of the resolution of the emulsions, over time, as the conductivity of the fluid is altered as the droplets coalesce to form larger droplets, and fall to the bottom of the cylinder 14.

Temperature can be controlled in a number of ways. The probe 10 and the sample of fluid can be immersed in a controlled temperature bath. A modification to the probe 10 can be made to include an internal heating/cooling coil 50, which circulates heated or cooled fluids through the probe to control the temperature. The heating or cooling fluids can be circulated by a pump 56. The pump 56 is external from the probe 10. The pump is controlled by a pump controller 66, preferably contained within the control box 20.

As noted above, many of the necessary components are preferably contained separate of the probe 10, and preferably are contained within a control box 20. This prevents the fluids from damaging many of the more delicate electrical parts. It also makes the parts more accessible and therefore easier to replace, if needed. Preferably contained within the control box 20 are all of the following: variable frequency generator 18, microphone amplifier 22, light source amplifier 38, light detector amplifier 40, conductivity bridge power source 44, conductivity bridge Wheatstone detector 46, thermistor voltage source 48, thermistor Wheatstone bridge 54, and pump controller 66. The pump 56 could also be contained within the control box 20.

The data-logger 24 used in this invention preferably has fourteen input channels, and can take information from several RTDs, pressure transducers, strain gauges, conductivity bridges, spectrometers, densitometers or other devices with linearized voltage output signals. The data-logger 24 also preferably has four output channels, which can be used to trigger such devices as servo motors, stepper motors, switches, electronic valves, telephone modems, and other interfaced devices. Through the use of pre-programmed triggers activated by results obtained from a particular analysis program, these output channels can instruct interfaced pumps, valves, or other devices to increase or decrease chemical treatment rates to optimize treatments. Further, with a modem program, updated information can be remotely obtained from the unit.

The probe 10 is constructed such that the speaker 12 and microphone 16 are contained in cavities 52 within the probe 10. Mylar film, which is molded within the epoxy, protects the electronics of each. The light pipes 32 and 34, heating/cooling coils 50, and thermistor 28 are preferably molded into the probe 10. The probe 10 can be submersed in a large number of harsh environments, if it is coated in a preferable material such as cured polyamino-bisphenyl-diepoxide material.

All of the various components comprising the device can be made small enough that the device can be fully portable. The control box 20 can be built into a corrosion-resistant box, such as an aluminum Haliburton case. Power in the field can be supplied in a number of different ways. The control box can have an AC power cord 60, if such power is available. It can also have a 12V DC plug 62, of appropriate size and shape to fit into an automobile cigarette lighter socket. And it can also be powered by batteries 64. In the preferred embodiment, all three of these alternatives are available in the control box 20. There are numerous other ways of delivering power to the various components of the device well known in the art.

Analysis of wax-containing systems provide a good example of the utility of this testing method. When the probe is immersed in a wax-containing system (e.g., hydrocarbon systems of varying molecular weights), and cooling fluid is circulated through the probes internal coils, the fluid within the probe cylinder will change physically as the wax (higher molecular weight fractions) begin to network. As the wax crystallizes, the voltage signal from the microphone will change. In addition to the sound signal change, the light transmission and cooling rate will change because of the solidification of the wax crystals. The cooling rate change is logged and later subjected to the enhances series of equations presented below. Emulsions are distinguished from wax containing systems by a combination of transmissivity change and an increase in conductivity as the water phase is freed from the oil phase. Waxy oils will not exhibit a conductivity increase as the oil is heated, unless they also contains an emulsion. The mathematical model is used on the wax analysis results, and the following empirically derived equations are used for conversion to fluid characteristics:

$$E.T. = T_{mp}^2 / C\#^{\log(c\#)} \qquad \text{Eq. I}$$

Where; $T_{mp}$=Melt point of carbon chain length C#normal paraffin E.T.=Elapsed cooling time ( seconds ) under prescribed cooling rate.

$$C\#_{calc.} = ((10)(T_{mp}^2/E.T.))^{0.5} \qquad \text{Eq. II}$$

$$T_{mp(calc.)} = ((E.T.)(C\#_{calc.}^{\log(C\#calc.)}))^{0.5} \qquad \text{Eq. III}$$

Where; $T_{mp(calc.)}$=Melt point of carbon chain length $C\#_{calc.}$ normal paraffin. At this point, we introduce some refinements to the above equations. Since each wax containing system is different, a constant must be introduced which relates empirically observed cooling rates to the theoretical rates represented in the above equations.

$$K' = (\log(T^2/E.T.))^{0.5}/((E.T./T^2) + 2.303) \qquad \text{Eq. IV}$$

Where; T=°K Measured and E.T.=Measured cooling time.

Because of this refinement, an estimated carbon number fraction can be obtained from the empirical measurements, and later compared to the theoretical value.

$$C\# = 10^{(k')((E.T./(Tmp \times Tmp)) + 2.303)} \qquad \text{Eq. V}$$

$$E.T. = ((T^2)(\log C\#))/((2.303)(k')(E.T.)(C\#^{\log C\#})) \qquad \text{Eq. VI}$$

$$G.C.\text{sim.dist.} = ((E.T._{calc.})(T) - E.T.)/(\text{sum dif.}(E.T._{calc.}(T) - E.T.)(100)) \qquad \text{Eq. VII}$$

Where; sum dif=Sum of the difference between $E.T._{calc.}(T)$–E.T. $G.C._{sim.dist.}$=Simulated distillation gas chromatograph.

The following additional calculations are used to transform frequency, voltage, resistance, velocity, and probe dimensions to units of viscosity (gram/centimeter seconds):

$$\text{gm/(cm.sec.)} = (F_s)(V_s^2)(v)/(R_s)(pir_2 1) \qquad \text{Eq. VIII}$$

Where; $F_s$=speaker frequency,
$v_s$=speaker voltage,
R=speaker resistance,
$pir^2 l$=probe cylinder volume,
v=velocity of sound in media.

$$\text{gm/(cm.sec.)} = (F_m)(V_m^2)(v)/(R_m)(pir^2 1) \qquad \text{Eq. XI}$$

Where; $F_m$=microphone frequency
$V_m$=microphone voltage
R=microphone resistance
$pir^2 l$=probe cylinder volume
v=sound velocity in media.

$$\text{Eq.IX}^2/\text{Eq.X}=\text{viscosity of the media.} \qquad \text{Eq. X}$$

From these calculations, it is possible to derive a characteristic spectrum for wax containing oils, and its behavior under differing heating, shear-rates, and cooling conditions.

In addition to the theoretically derived model characteristics, empirical information can also be obtained by running the strip-chart recorder. Demulsification characteristics are best obtained in this fashion.

Obviously, the inventive testing equipment can also be used to evaluate fluids with other troublesome characteristics, such as scale tendencies or asphaltene content. Numerous other uses of the inventive testing equipment will be obvious to those skilled in the art.

The following examples show some of the capabilities of the invention:

EXAMPLE I

An oil well that produced 4,500 barrels of oil per day when it was first brought in, and 4,500 barrels after tubing and well-bore clean-up, would drop to 0 barrels per day after 17–20 days production. Engineers thought the trouble was asphaltene build-up, and would close the well to perform a tubing and wellbore clean-up. This cost the producing company $120,000 over a 60 day period. The production fluid was tested in the above described invention. By observing the changes in voltage, light transmittal, and sonic properties. The problem was determined to be caused by paraffin wax build-up. A crystal modifier product, which was selected based on the wax characteristics of the tested fluid, was added to the well at a dose rate of 300 parts per million (based on oil production) for a 60 day period. The well dropped from 4,500 barrels per day to 2,500 barrels per day after 60 days. This resulted in a savings to the production company of over $1,200,000 over the 60 day period.

EXAMPLE II

A synthetic emulsion was produced by mixing cooking oil and water. The probe was then immersed in the emulsion, while measuring sound voltage, temperatures (both the surrounding environment and within the sample itself), and conductivity. Then through a number of tests, a detergent that was known to be able to break the emulsion was then added to the sample in various amounts. When sufficient detergent was added, there was a resulting decrease in conductivity, and increase in sound voltage, thereby allowing a determination of how much detergent was required to break the emulsion.

EXAMPLE III

An offshore well had been confirmed, by conventional testing methods, to have a combination water-in-oil emulsion and wax problem. Observation of the fluid showed that there was an emulsion, and testing of the well fluids in the inventive device confirmed that there was a wax problem. Product screening of variously treated fluid samples was conducted on the invention, and an optimized combination emulsion breaker/wax crystal modifier product was chosen. This was possible because the invention can back calculate the formulation of a wax crystal modifier product from the mathematical model described above.

The combination product was continuously added to the well at 300 parts per million based on production. Prior to the treatment, the fluids would often fail sales criteria for water content, and pour point. After the treatment, the fluids have been shipped without fail for a one year period.

The invention is a significant improvement over conventional testing equipment and methods. It is compact, taking less than 6 square feet of bench space. It is portable, weighing less than 25 pounds, and it is faster, since it can be brought to the problem area.

It will be understood that the preferred embodiment of the invention described above is shown as an illustration and not as a limitation of the invention. The principles and features of this invention may be employed in varied and numerous embodiments without departing from the scope of the invention.

I claim:

1. Fluid testing equipment for selecting optimized wax crystal modifiers for use in a waxy crude, said equipment comprising:

a variable frequency generator;

speaker, electrically connected to said variable frequency generator, for broadcasting sound waves through a sample of said waxy crude to be tested;

means for altering the temperature of said sample through a range of temperature from above said waxy crude's initial cloud point to a lower temperature at which all of the wax in said waxy crude is no longer in solution in said crude, said speaker broadcasting continuously as said sample is cooled through said range of temperature;

a microphone, positioned in proximity to said speaker, so that said microphone can receive said sound waves from said speaker;

a microphone amplifier, electrically connected to said microphone, to amplify an electrical signal from said microphone;

a sonic output device, electrically connected to said microphone amplifier; and a probe, comprising a casing and a sample cavity, defined by the walls of said casing and an upper and lower endplate, and wherein said speaker is contained within said casing, proximate to said cavity, and wherein said microphone is contained within said casing, proximate to said cavity.

2. The fluid testing equipment of claim 1, wherein said cavity is coated in mylar.

3. The fluid testing equipment of claim 1, wherein said casing is coated with an impermeable, corrosion resistant coating.

4. The fluid testing equipment of claim 1, wherein said speaker and said microphone are on opposite sides of said cavity.

5. The fluid testing equipment of claim 4, further comprising:

a conductivity bridge, positioned within said cavity, to measure the conductivity of a sample fluid;

a conductivity power source, electrically connected to said conductivity bridge;

a conductivity Wheatstone bridge, electrically connected to said conductivity bridge; and, a conductivity output device, electrically connected to said conductivity Wheatstone bridge.

6. The fluid testing equipment of claim 5, further comprising:

a source light pipe, positioned adjacent to said cavity, such that one end of said source light pipe can transmit light into said cavity;

an LED source, positioned within said casing and connected to said source light pipe at the end of said source light pipe opposite said cavity, to generate said light that travels through said source light pipe and into said cavity;

a light detector pipe, positioned adjacent to said cavity, and positioned across said cavity from said source light pipe, such that one end of said light detector pipe can receive light from said source light pipe after said light crosses said cavity;

a light detector, positioned within said casing, and connected to said light detector pipe at the end opposite said cavity;

a light output device, connected electrically to said light detector;

wherein said means for altering temperatures comprises heating/cooling lines, positioned within said casing in proximity to said cavity, said lines starting and ending outside of said casing, connectable to a source of hot or cold fluid, to provide heating or cooling to the cavity;

a thermistor, positioned within said casing and proximate to said cavity, said thermistor to provide temperature readings;

a thermistor power source, electrically connected to said thermistor, to provide electrical current to said thermistor;

a thermistor Wheatstone bridge, electrically connected to said thermistor, to received electrical signals from said thermistor and convert said signals to digital format;

a thermistor output device, electrically connected to said thermistor Wheatstone bridge, to output said signals received from said thermistor Wheatstone bridge.

7. The fluid testing equipment of claim 6, further comprising a control box, said control box comprising:

a box to house the contents of said box, said contents comprising said microphone amplifier, said conductivity power source, said conductivity Wheatstone bridge, said light output device, said thermistor power source, said thermistor Wheatstone bridge;

a LED power source, contained within said box, electrically connected to said LED source, said LED power source to provide power to said LED source;

a light amplifier, contained within said box, connected electrically between said light detector pipe and said light output device;

a sonic power source, contained within said box, said sonic power source electrically connected to said variable frequency generator, said sonic power source providing power to said variable frequency generator.

8. The fluid testing equipment of claim 6, further comprising:

a light amplifier connected electrically between said light detector pipe and said light output device; and, a data-logger, electrically connected to said microphone amplifier, said light detector amplifier, said conductivity Wheatstone bridge, and said thermistor Wheatstone bridge, to allow the output signals from said microphone amplifier, said light detector amplifier, said conductivity Wheatstone bridge, and said thermistor Wheatstone bridge to be recorded.

9. The fluid testing equipment of claim 8, further comprising:

a computer, electrically connected to said data-logger, to allow output signals of said data-logger to be recorded and analyzed.

10. The fluid testing equipment of claim 6, further comprising:

a light amplifier connected electrically between said light detector pipe and said light output device; and, a computer, electrically connected to said microphone amplifier, said light detector amplifier, said conductivity Wheatstone bridge, and said thermistor Wheatstone bridge, to allow the output signals from said microphone amplifier, said light detector amplifier, said conductivity Wheatstone bridge, and said thermistor Wheatstone bridge to be recorded and analyzed.

11. The fluid testing equipment of claim 6, further comprising:

a light amplifier connected electrically between said light detector pipe and said light output device; and, a printer, electrically connected to said microphone amplifier, said light detector amplifier, said conductivity Wheatstone bridge, and said thermistor Wheatstone bridge, to allow the output signals from said microphone amplifier, said light detector amplifier, said conductivity Wheatstone bridge, and said thermistor Wheatstone bridge to be recorded.

12. The fluid testing equipment of claim 6, wherein said cavity is coated in mylar, and wherein said casing is coated with an impermeable, corrosion resistant coating, said fluid testing equipment further comprising:

a control box, said control box comprising:

a box to house the contents of said box, said contents comprising said microphone amplifier, said conductivity power source, said conductivity Wheatstone bridge, said light output device, said thermistor power source, said thermistor Wheatstone bridge;

a LED power source, contained within said box, electrically connected to said LED source, said LED power source to provide power to said LED source;

a light amplifier, contained within said box, connected electrically between said light detector pipe and said light output device; and a sonic power source, contained within said box, said sonic power source electrically connected to said variable frequency generator, said sonic power source providing power to said variable frequency generator;

a pump, said pump connected to said heating/cooling lines, to circulate said hot or cold fluids;

a pump controller, electrically connected to said pump and a pump power source, to control the flow rate through said pump;

a data-logger, electrically connected to said microphone amplifier, said light amplifier, said conductivity Wheatstone bridge, and said thermistor Wheatstone bridge, to allow the output signals from said microphone amplifier, said light detector amplifier, said conductivity Wheatstone bridge, and said thermistor Wheatstone bridge to be recorded; a printer, electrically connected to said data-logger, to allow the output signals from said data-logger to be recorded; and a computer, electrically connected to said data-logger, to allow output signals of said data-logger to be recorded and analyzed.

13. The fluid testing equipment of claim 4, further comprising:

a source light pipe, positioned adjacent to said cavity, such that one end of said source light pipe can transmit light into said cavity;

an LED source, positioned within said casing and connected to said source light pipe at the end of said source light pipe opposite said cavity, to generate said light that travels through said source light pipe and into said cavity;

a light detector pipe, positioned adjacent to said cavity, and positioned across said cavity from said source light pipe, such that one end of said light detector pipe can receive light from said source light pipe after said light crosses said cavity;

a light detector, positioned within said casing, and connected to said light detector pipe at the end opposite said cavity;

a light output device, connected electrically to said light detector.

14. The fluid testing equipment of claim 4, further comprising:

heating/cooling lines, positioned within said casing in proximity to said cavity, said lines starting and ending outside of said casing, connectable to a source of temperature-modifying fluids, to provide temperature modification to the cavity.

15. The fluid testing equipment of claim 14, further comprising a pump, said pump connected to said heating/cooling lines, to circulate said temperature-modifying fluids.

16. The fluid testing equipment of claim 15, further comprising a pump controller, electrically connected to said pump and a pump power source, to control the flow rate through said pump.

17. The fluid testing equipment of claim 4, further comprising:

a thermistor, positioned within said casing and proximate to said cavity, said thermistor to provide temperature readings; a thermistor power source, electrically connected to said thermistor, to provide electrical current to said thermistor;

a thermistor Wheatstone bridge, electrically connected to said thermistor, to received electrical signals from said thermistor and convert said signals to digital format;

a thermistor output device, electrically connected to said Wheatstone bridge, to output said signals received from said Wheatstone bridge.

* * * * *